US009035079B2

(12) United States Patent
Brandhorst et al.

(10) Patent No.: US 9,035,079 B2
(45) Date of Patent: May 19, 2015

(54) METHOD FOR CLEAVING UNSATURATED FATTY CHAINS

(71) Applicant: Arkema France, Colombes (FR)

(72) Inventors: Markus Brandhorst, Lyons (FR); Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/361,391

(22) PCT Filed: Nov. 22, 2012

(86) PCT No.: PCT/FR2012/052686
§ 371 (c)(1),
(2) Date: May 29, 2014

(87) PCT Pub. No.: WO2013/079849
PCT Pub. Date: Jun. 6, 2013

(65) Prior Publication Data
US 2014/0357880 A1    Dec. 4, 2014

(30) Foreign Application Priority Data

Dec. 1, 2011  (FR) ..................... 11 61035

(51) Int. Cl.
*C07C 51/285* (2006.01)
*C07C 51/21* (2006.01)
*C07C 253/22* (2006.01)
*C07C 253/30* (2006.01)

(52) U.S. Cl.
CPC ............... *C07C 51/285* (2013.01); *C07C 51/21* (2013.01); *C07C 253/22* (2013.01); *C07C 253/30* (2013.01); *C07C 2523/30* (2013.01)

(58) Field of Classification Search
None
See application file for complete search history.

(56) References Cited

U.S. PATENT DOCUMENTS

| | | | |
|---|---|---|---|
| 5,714,623 A * | 2/1998 | Sabarino et al. | ............... 554/132 |
| 5,939,572 A | 8/1999 | Sibi et al. | |
| 6,005,134 A | 12/1999 | Terasaka et al. | |
| 6,680,395 B2 | 1/2004 | Springer | |
| 6,696,582 B2 | 2/2004 | Springer et al. | |
| 6,800,783 B2 | 10/2004 | Springer et al. | |
| 7,138,544 B2 | 11/2006 | Springer et al. | |
| 7,799,945 B2 | 9/2010 | Springer | |
| 7,812,186 B2 * | 10/2010 | Bastioli et al. | ................. 554/138 |
| 8,222,438 B2 * | 7/2012 | Bastioli et al. | ................. 554/132 |
| 8,664,434 B2 | 3/2014 | Weber et al. | |

FOREIGN PATENT DOCUMENTS

| | | | | |
|---|---|---|---|---|
| FR | 2769624 | * | 4/1999 | ............. C07C 51/235 |
| FR | 2769624 A | | 3/2000 | |
| GB | 641955 | | 8/1950 | |
| GB | 741739 | * | 12/1955 | |
| JP | 10195035 A | | 7/1990 | |
| JP | 2000007637 | | 1/2000 | |
| JP | 2000016977 A | | 2/2009 | |
| WO | WO 96/39373 | * | 12/1996 | ............. C07C 51/16 |
| WO | WO96/39376 | | 12/1996 | |

* cited by examiner

*Primary Examiner* — Yate K Cutliff
(74) *Attorney, Agent, or Firm* — Steven D. Boyd

(57) ABSTRACT

The invention relates to a method for cleaving unsaturated fatty chains comprising a step of oxidative cleavage in which at least one fatty acid derivative having at least one unsaturation is reacted in the liquid phase with hydrogen peroxide in the presence of a catalyst for activating the reaction of oxidative cleavage and of molecular oxygen and in the absence of organic solvent.

24 Claims, No Drawings

METHOD FOR CLEAVING UNSATURATED FATTY CHAINS

This application claims priority to and is the national phase under 35 USC §371 of prior PCT International Application Number PCT/FR2012/052686 filed Nov. 22, 2012 which designated the United States of America and claimed priority to French Patent Application serial number 11.61035 filed Dec. 1, 2011, all incorporated herein by reference.

The work that led to this invention received financing from the European Union within the scope of the 7th Framework Program (FP7/2007-2013) under project number No. 241718 EUROBIOREF.

FIELD OF THE INVENTION

The present invention relates to a method for cleaving unsaturated fatty chains as well as to the use of said method for the synthesis of amino acids, dinitriles, diamines, diacids of polyesters and/or of polyamides.

The invention notably relates to a method of synthesis of ω-functionalized acids of formula R—$(CH_2)_n$—COOH or R—$(CH_2)_n(CH=CH)_m$—COOH in which R represents COOH or $NH_2CH_2$ comprising a step of oxidative cleavage of an unsaturated fatty acid derivative, also called "fatty acid derivative having at least one unsaturation".

"Unsaturated fatty acid derivative" or "fatty acid derivative having at least one unsaturation" means a cis or trans unsaturated compound comprising between 7 and 24 carbon atoms selected from an unsaturated fatty acid—whether it is in acid form, simple or "complex" ester, such as triglyceride or ester of fatty acid and fatty alcohol (vegetable wax)—or an unsaturated fatty nitrile, said fatty acid derivative being obtained if necessary from a saturated or unsaturated hydroxylated fatty acid.

"Hydroxylated fatty acid" means a fatty acid comprising at least one hydroxyl function, comprising between 7 and 24 carbon atoms, saturated or unsaturated—whether it is in acid form, simple or "complex" ester, such as triglyceride or ester of fatty acid and fatty alcohol (vegetable wax or estolide)—.

Thus, when said unsaturated fatty acid derivative is an acid, the step of oxidative cleavage leads to an ω-functionalized diacid of formula HOOC—$(CH_2)_n$—COOH or HOOC—$(CH_2)_n(CH=CH)_m$—COOH.

When said unsaturated fatty acid derivative is a nitrile, the step of oxidative cleavage leads to the formation of a nitrile-fatty acid, which, after hydrogenation of its nitrile function and of any remaining unsaturations, leads to an r-functionalized acid of formula $NH_2CH_2$—$(CH_2)_n$—COOH or $NH_2CH_2$—$(CH_2)_{n+2m}$—COOH.

The nitrile-fatty acids of general formula NC—$(CH_2)_n$—COOH or of formula NC$(CH_2)_n(CH=CH)_m$COOH (empirical formula $C_{n+2m+2}H_{2n+2m+1}NO_2$) in the case when cleavage is effected on a polyunsaturated fatty nitrile, called hereinafter "heminitriles of diacids" or more simply "heminitriles", are intermediates usable in the synthesis of a whole range of "fatty" compounds such as ω-amino acids, α-ω-dinitriles, α-ω-diamines, α-ω-diacids. "Nitrile fatty acid" means linear compounds having from 6 to 15 carbon atoms.

TECHNICAL BACKGROUND

Oxidative cleavage of unsaturated fatty chains is a widely used technique for preparing carboxylic acids from olefinic hydrocarbon chains.

This method typically consists of cleaving the double bond of an unsaturated fatty acid by means of a strong oxidant for passing from a long-chain unsaturated fatty acid to two reduced chain saturated fatty molecules, one α-ω bifunctional and the other monofunctional.

A major problem encountered when applying this method is the high viscosity of the medium, which prevents good mass transfer. To rectify this, the methods of the prior art are most often applied in two steps and/or in an organic solvent medium.

In the methods in two steps, the first step consists of oxidation of the double bond to form a vicinal diol. The second step consists of rupture of the carbon-carbon bond between the two hydroxyl functions to obtain said reduced chain saturated fatty molecules.

We may mention document WO2008/138892, which teaches a method of manufacturing saturated monocarboxylic acids and triglycerides of saturated carboxylic acids having at least one acid function, starting from unmodified vegetable oils containing triglycerides of fatty acids. This method comprises two separate steps: the first step consists of reacting the triglycerides of fatty acids with an oxidizing agent in the presence of a catalyst to obtain a vicinal diol. The second step consists of reacting the vicinal diol with oxygen in the presence of a catalyst of oxidation of the reaction of transformation of the two hydroxyl functions into carboxylic acid functions.

Such a two-step method is not, however, optimum for application on an industrial scale. On the one hand, the use of two different catalysts is expensive. On the other hand, it is restricting to carry out two separate steps, notably because it is necessary to perform a reactor transfer.

WO2007/039481 and WO94/10122 also teach methods of oxidative cleavage of unsaturated fatty chains in two steps using a different catalyst in each step. The starting compounds are unsaturated fatty acids or derivatives thereof, for example their esters.

In the methods carried out in an organic solvent medium, it is only possible to use a low content of hydrogen peroxide (generally less than or equal to 30 wt % relative to the total weight of the liquid phase) as the simultaneous use of oxygen and of a light organic solvent such as an alcohol has a risk of leading to the formation of an explosive gas mixture of the organic solvent and oxygen.

We may mention document U.S. Pat. No. 5,939,572, which teaches a method of preparing carboxylic acid comprising a step of bringing an olefinic compound or a vicinal dialcohol into contact with oxygen in the presence of a polar protic solvent, an inorganic oxide catalyst (selected from the oxides of tungsten, molybdenum, niobium, vanadium, tantalum, titanium, yttrium) and a peroxidant such as hydrogen peroxide or a peralkanoic acid.

We may also cite application WO96/39376, which describes the co-injection of a dilute solution of $H_2O_2$ and molecular oxygen in the presence of various catalysts in an organic solvent medium.

Besides the safety problems mentioned, the use of solvents is likely to cause difficulties environmentally, notably for complying with the regulations relating to limitation of volatile organic compounds (VOCs), or in terms of waste recycling.

There is therefore a need for a method for cleaving unsaturated fatty chains that avoids the aforementioned drawbacks, at least partially. Notably, it is desirable to have a method for obtaining both heminitriles and diacids. It is desirable to have a method that does not use organic solvent. It is desirable to have a method having a good yield of cleavage products. It is desirable to have a method that limits the proportion of reaction byproducts, notably those of the oxo-nitrile and aldehyde type, thus increasing the selectivity of the reaction. Finally, it is desirable to have a method that limits the amount of reagents required (notably hydrogen peroxide) and/or of effluents generated.

SUMMARY OF THE INVENTION

Thus, the present invention relates to a method for cleaving unsaturated fatty chains, comprising a step of oxidative cleavage in which at least one fatty acid derivative having at least one unsaturation (hereinafter: unsaturated fatty acid derivative) is reacted in the liquid phase with hydrogen peroxide in the presence of a catalyst for activating the reaction of oxidative cleavage and of molecular oxygen and in the absence of organic solvent.

In a first variant of the method according to the invention, the unsaturated fatty acid derivative is selected from: a fatty acid, a fatty acid ester, a triglyceride, an ester of fatty acid and fatty alcohol or mixtures thereof, so as to obtain at least one diacid at the end of said oxidative cleavage step.

In a second variant of the method according to the invention, the unsaturated fatty acid derivative is a fatty nitrile corresponding to the formula:

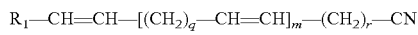
$$R_1-CH=CH-[(CH_2)_q-CH=CH]_m-(CH_2)_r-CN$$

where $R_1$ is H or an alkyl radical comprising from 1 to 11 carbon atoms comprising if necessary a hydroxyl function and/or a terminal nitrile function,
q, m and r are integral indices such that q=0 or 1, 0≤m≤2 and 4≤r≤13,
or mixtures thereof,
so as to obtain, at the end of said oxidative cleavage step, at least one nitrile-acid of formula:

$$HOOC-R'-CN$$

where R' is an alkyl radical comprising from 4 to 13 carbon atoms or an alkylene radical comprising from 4 to 13 carbon atoms and from 0 to 2 unsaturations (inclusive).

In the case when $R_1$ bears a terminal nitrile function, preferably m=0, i.e. the fatty nitrile is preferably monounsaturated.

In the case when $R_1$ bears a terminal nitrile function, the molecule of the fatty nitrile is preferably symmetric, which makes it possible to obtain two identical products at the end of the oxidative cleavage step.

The invention also relates to the use of said method for cleaving unsaturated fatty chains for the synthesis of amino acids, dinitriles, diamines, diacids of polyesters and/or of polyamides.

"Fatty nitrile comprising at least one unsaturation" in the sense of the invention (hereinafter: unsaturated fatty nitrile), means a fatty chain bearing one or even two mono- or poly-unsaturated nitrile functions, preferably comprising between 7 and 24 carbon atoms per molecule.

"Oxidative cleavage" means the reaction by which at least one unsaturation of the unsaturated fatty acid derivative is oxidized and cleaved to obtain two molecules bearing a carbonyl function, whether it is carboxylic acid or aldehyde, on each of the carbon atoms initially joined together by said unsaturation. Preferably, the reaction of oxidative cleavage is employed in order to obtain the molecules bearing an acid function, but the molecules bearing an aldehyde function can also be obtained as side products and/or intermediates.

"Catalyst for activating the reaction of oxidative cleavage" means a catalyst capable of catalyzing said reaction of oxidative cleavage.

The oxidative cleavage step is carried out in the absence of organic solvent. "Solvent" means, in the sense of the invention, a chemical substance capable of dissolving within it, compounds that are normally mutually immiscible, so as to allow their coexistence within one and the same phase. Thus, in the method according to the invention, the liquid phase where the reaction takes place remains two-phase, containing an aqueous phase comprising hydrogen peroxide and the catalyst, and an organic phase comprising the unsaturated fatty acid derivative. Oxygen and the catalyst are distributed in the two phases as a function of the partition coefficients.

"Liquid phase" means the liquid medium consisting of the aqueous phase and the organic phase.

The method according to the invention offers many advantages. It can be used both on unsaturated fatty acids (simple or complex) and unsaturated fatty nitriles, optionally obtained simply, starting from saturated or unsaturated, hydroxylated fatty acids.

The method according to the invention thus makes it possible to obtain both diacids and heminitriles, starting from which it will be possible to synthesize amino acids for manufacturing polyamides if required, dinitriles for manufacturing diamines if required, or else diacids for manufacturing polyamides or polyesters if required.

Surprisingly, the inventors discovered that the introduction of molecular oxygen ($O_2$) in a two-phase liquid reaction mixture for carrying out a reaction of oxidative cleavage on a fatty acid derivative using activated hydrogen peroxide greatly improves the yield of cleavage products, advantageously of heminitriles or of diacids, according to one or other of the variants of the method.

Moreover, carrying out the reaction of oxidative cleavage in a single step notably simplifies the application of the method on an industrial scale, in comparison with the known methods.

The method according to the invention additionally has the advantage of reducing the level of byproducts of the reaction of oxidative cleavage, such as oxo-nitriles and aldehydes.

Advantageously, the method according to the invention is carried out in the absence of organic solvent, which limits the risk of explosion as well as the amount of VOCs and effluents generated.

The method according to the invention is also effective for limiting the consumption of hydrogen peroxide.

DETAILED DESCRIPTION

The invention will now be described in more detail and non-exhaustively in the description given hereunder.

When reference is made to ranges, expressions of the type "ranging from . . . to" include the limits of the range. Conversely, expressions of the type "between . . . and . . . " exclude the limits of the range.

Unless stated explicitly, the percentages expressed are percentages by weight.

Unless stated otherwise, the parameters to which reference is made are measured at atmospheric pressure.

Obtaining the Unsaturated Fatty Acid Derivative

According to one embodiment of the invention, the unsaturated fatty acid derivative comprises one, two, or even three unsaturations. Preferably, it comprises a single unsaturation. This makes it possible to limit the amount of hydrogen peroxide consumed in the reaction of oxidative cleavage.

According to one embodiment of the invention, the unsaturated fatty acid derivative is of natural origin, i.e. of vegetable origin (which includes the algae) or animal origin.

According to the first variant of the method of the invention, the unsaturated fatty acid derivative is selected from: a fatty acid, a fatty acid ester, a triglyceride, an ester of fatty acid and fatty alcohol or mixtures thereof, so as to obtain at least one diacid at the end of said oxidative cleavage step. The step of oxidative cleavage can comprise, if necessary, hydrolysis of the bifunctional compound resulting from the reaction of oxidative cleavage as such to obtain the diacid (this is for example the case of an ester-acid obtained by oxidative cleavage of a fatty acid ester).

As unsaturated fatty acid more particularly suitable for application of the invention, we may mention:
  petroselinic acid (cis-6-octadecenoic acid), its derivative 6-heptenoic acid obtained by ethenolysis, α-linolenic acid (6-9-12-octadecatrienoic), these acids being obtainable from coriander for example;
  cis-8-eicosenoic acid, cis-5,8,11,14-eicosatrienoic acid (arachidonic acid), ricinoleic acid which gives after dehydration conjugated 8,10-octadecadienoic acid;
  caproleic acid (cis-9-decenoic), palmitoleic acid (cis-9-hexadecenoic), myristoleic acid (cis-9-tetradecenoic), oleic acid (cis-9-octadecenoic), 9-decenoic acid obtained by ethenolysis of an oleic acid for example, elaidic acid (trans-9-octadecenoic), ricinoleic acid (12-hydroxy-cis-9-octadecenoic), gadoleic acid (cis-9-eicosenoic), linoleic acid (9-12-octadecadienoic), rumenic acid (9-11-octadecadienoic), conjugated linoleic acid (9-11-octadecadienoic), these acids being obtainable from sunflower, colza, castor, olive, soya, palm, flax, avocado, sea buckthorn, coriander, celery, dill, carrot, fennel, Limnanthes (meadowfoam);
  conjugated 10-12 linoleic acid (10-12-octadecadienoic), 10-undecylenic acid obtained by thermal cracking of the methyl ester of ricinoleic acid for example;
  vaccenic acid (cis-11-octadecenoic), gondoic acid (cis-11-eicosenoic), lesquerolic acid (14-hydroxy-cis-11-eicosenoic), ketoleic acid (cis-11-docosenoic), which can be obtained from *Lesquerella* oil (lesquerolic oil), oil of *Camelina sativa* (gondoic oil), oil from a plant of the family sapindaceae, fish oil, oils from microalgae (ketoleic oil), conjugated linoleic acid (9-11-octadecadienoic), itself obtained for example by dehydration of ricinoleic acid;
  12-octadecenoic acid (cis or trans) obtained for example by dehydration of 12-hydroxystearic acid, conjugated 10-12 linoleic acid (10-12-octadecadienoic), 12-tridecenoic acid obtained for example by thermal cracking of the ester (notably methyl ester) of lesquerolic acid;
  erucic acid (cis-13-docosenoic) and brassidic acid (trans-13-docosenoic), which can for example be obtained from erucic colza, from honesty or from *Crambe maritima* (sea kale), 13-eicosenoic acid (cis or trans) obtained for example by dehydration of 14-hydroxyeicosanoic acid, which in its turn can be obtained by hydrogenation of lesquerolic acid;
  14-eicosenoic acid (cis or trans) obtained for example by dehydration of 14-hydroxyeicosanoic acid, itself obtained by hydrogenation of lesquerolic acid; nervonic acid (cis-15-tetracosoic), which can be obtained from *Malania oleifera* and from honesty (*Lunaria annua* also known by the name honesty or money plant);
  or their cis and trans isomers,
  or mixtures thereof.

Among the aforementioned unsaturated fatty acid derivatives, there may be an advantage in selecting, in the order of availability, a δ-9, δ-13, δ-11 unsaturated fatty acid derivative (i.e. with the double bond in position 9, 11 or 13 relative to the acid function) as they are the most abundantly available. Nevertheless, in order of preference, fatty acids will be selected having a double bond in position 11 or more, and preferably in position 11 or 12 or leading to unsaturated nitriles having a double bond in position 11 or more, and preferably in position 11 or 12.

Preferably, when vaccenic acid is used, the latter is of natural origin, i.e. of vegetable origin (which includes the algae) or of animal origin. In a preferred embodiment, the invention relates to a method of oxidative cleavage of an unsaturated fatty nitrile obtained from vaccenic acid of natural origin, in order to obtain the corresponding heminitrile.

The following routes can be adopted for preparing a vaccenic acid of natural origin:
  vaccenic acid can be obtained directly from plants, in particular by extraction, from mango pulp, from sea buckthorn, from sea buckthorn oil, or from animal derivatives such as butter,
  vaccenic acid can also be obtained by genetically modifying plants, such as safflower, camelina, or else *Arabidopsis thaliana* as is described in the article of Nguyen et al., Plant physiology, December 2010, Vol. 154, pp 1897-1904,
  vaccenic acid can be obtained from genetically modified bacteria or yeasts, for example *Escherichia coli* as is described in the article of Mendoza et al., Journal of bacteriology September 1982, pp 1608-1611,
  a last route for obtaining vaccenic acid is dehydration or else ammoniation of 12-hydroxystearic acid.

Preferably, when gondoic acid is used, the latter is of natural origin, i.e. of vegetable origin (which includes the algae) or of animal origin. In a preferred embodiment, the invention relates to a method of oxidative cleavage of an unsaturated fatty nitrile obtained from gondoic acid of natural origin, in order to obtain the corresponding heminitrile.

The following routes can be adopted for preparing a gondoic acid of natural origin:
  gondoic acid (cis-11-eicosenoic) can be obtained directly from plants, in particular by extraction, from oil of *Camelina* (*Camelina sativa*), which contains more than 15% of gondoic acid, from colza oil rich in erucic acid, from crambe, from honesty which generally contain from 2 to 15% of gondoic acid, from *Allysum martimum* (gondoic acid content of 41.8%), from *Selenia grandis* (gondoic acid content of 58.5%), from *Marshallia caespitose* (gondoic acid content of 43.9%),
  gondoic acid can also be obtained by genetically modifying plants, such as camelina, or else *Arabidopsis thaliana*,
  gondoic acid can be obtained from genetically modified bacteria or yeasts, for example *Escherichia coli*,
  a last route for obtaining gondoic acid is hydrolysis of jojoba oil, which is in fact a vegetable wax (called oil because the wax is liquid at room temperature). This wax is composed essentially of esters of long-chain fatty acid and of long-chain fatty alcohols. Gondoic acid represents more than 60%, or even 70% of the fatty acids present in the wax.

The aforementioned fatty acids can be isolated by means known by a person skilled in the art such as molecular distillation, including short-path, crystallization, liquid-liquid extraction, complexation with urea, including extraction with supercritical $CO_2$, or a combination of these means.

The esters of the aforementioned fatty acids can be used as esters of unsaturated fatty acid more particularly suitable for carrying out the invention.

As unsaturated triglyceride more particularly suitable for carrying out the invention, we may mention: a vegetable oil comprising a mixture of triglycerides of unsaturated fatty acids such as oil of sunflower, colza, castor, *lesquerella*, *cam-*

*elina*, olive, soya, palm, sapindaceae in particular of avocado, sea buckthorn, coriander, celery, dill, carrot, fennel, mango, Limnanthes alba (meadowfoam) and mixtures thereof; microalgae; animal fats.

As an example of unsaturated wax suitable for carrying out the invention, we may mention jojoba oil.

According to one embodiment, the method of the invention further comprises a step of manufacturing the fatty acid derivative starting from a hydroxylated saturated fatty acid that can be in simple or complex form (ester, triglyceride, wax). Said manufacturing step comprises dehydration of said hydroxylated saturated fatty acid to unsaturated fatty acid. The unsaturated fatty acid obtained can be submitted directly to the step of oxidative cleavage according to the first variant of the method according to the invention. It can also be submitted to an additional nitrilation step leading to an unsaturated fatty nitrile able to undergo the step of oxidative cleavage, according to the second variant of the method according to the invention.

According to this same embodiment, the method of the invention can further comprise, upstream, a step of manufacturing said hydroxylated saturated fatty acid starting from an unsaturated hydroxylated fatty acid that can be in simple or complex form (ester, triglyceride, wax). This manufacturing step comprises hydrogenation of the unsaturated hydroxylated fatty acid to obtain a hydroxylated saturated fatty acid.

As hydroxylated saturated fatty acid particularly suitable for carrying out the invention, we may mention 12-hydroxylauric acid, 14-hydroxymyristic acid (both obtained for example by fermentation of lauric and myristic acids), 12-hydroxystearic acid (obtained for example by hydrogenation of ricinoleic acid and/or densipolic acid), 14-hydroxyeicosanoic acid (obtained for example by hydrogenation of lesquerolic acid and/or auricolic acid), or mixtures thereof.

As unsaturated hydroxylated fatty acid more particularly suitable for carrying out the invention, we may mention: ricinoleic acid (12-hydroxy-cis-9-octadecenoic), lesquerolic acid (14-hydroxy-cis-11-eicosenoic), densipolic acid and auricolic acid, or mixtures thereof.

Hydrogenation can advantageously be carried out at a temperature ranging from 70° C. to 150° C., preferably ranging from 90° C. to 130° C.

Hydrogenation can advantageously be carried out at a pressure of dihydrogen ranging from 1 to 300 bar, preferably from 5 to 50 bar.

Hydrogenation can be carried out in the presence of a homogeneous or heterogeneous hydrogenation catalyst. The latter can be selected from a precious metal such as Pt, Pd or Rh, a transition metal such as Mo, W, Cr, Fe, Co, Ni, used alone or mixed, optionally deposited on a support comprising for example an activated charcoal, alumina or silica. Preferably, the hydrogenation catalyst is a Raney nickel or a metal deposited on activated charcoal.

Dehydration of the hydroxylated saturated fatty acid can advantageously be carried out at a temperature ranging from 200° C. to 300° C.

Dehydration can advantageously be carried out in the presence of an acid catalyst, preferably selected from sulfuric acid, phosphoric acid, sulfonic acid, an alkylsulfonate or mixtures thereof.

According to a variant of this embodiment, in the case when the fatty acid derivative that is used in the step of oxidative cleavage is a fatty nitrile, it is possible to omit the step of dehydration of the hydroxylated saturated fatty acid, instead having it undergo a nitrilation and a concomitant dehydration.

This embodiment advantageously makes it possible to obtain a very "clean" nitrile, comprising for example more than 85 wt % of monounsaturated nitrile relative to the weight of the nitrilation products.

The reaction of nitrilation (or ammoniation, the two terms being used indiscriminately) of the fatty acids by means of ammonia is well known and follows the following simplified reaction scheme:

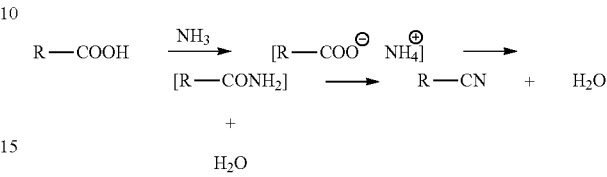

Nitrilation can be carried out in the liquid phase (batch process) or in the gas phase (continuous process) using ammonia at a temperature generally between 150° C. and 350° C. with a catalyst.

Liquid-phase nitrilation can be carried out at a temperature between about 150° C. (first step) and 250°-300° C. (second step) with a catalyst, which is generally a metal oxide and most often zinc oxide.

Gas-phase nitrilation can be carried out at high temperature levels and generally on a catalyst consisting of a fixed bed of doped or non-doped alumina. The fatty acid is vaporized in the presence of a large amount of ammonia, the excess of which is recycled. The process can therefore be carried out in the gas phase with a fixed bed of doped or non-doped alumina as catalyst.

In gas-phase nitrilation, a great many other catalysts can be used and there is abundant literature on this subject. We may mention for example document JP200016977, which describes catalysis with niobium oxide at a temperature of 260° C. (stearic acid), document JP20007637, which describes a process carried out at a temperature ranging from 180° to 350° C. also with a catalyst of the niobium oxide type, U.S. Pat. No. 6,005,134, which describes catalysis with titanium and finally patent JP10195035, which describes catalysis with iron-doped zirconium oxide.

Carrying out nitrilation using urea or cyanuric acid as agent is also known from GB641955. It is also possible to use any other source of ammonia.

In the case when the unsaturated fatty acid derivative that is used in the step of oxidative cleavage is an unsaturated fatty nitrile, those obtained at least partially from natural unsaturated fatty acids or esters are preferred. Thus, according to one embodiment, the method of the invention comprises a step of manufacturing said fatty nitrile starting from an unsaturated fatty acid or ester of natural origin of formula:

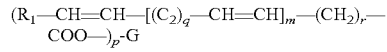

where $R_1$ is H or an alkyl radical comprising from 1 to 11 carbon atoms if necessary comprising a hydroxyl function and/or a terminal nitrile function, G is H, an alkyl radical with 1 to 11 carbon atoms or a radical comprising 2 or 3 carbon atoms bearing 1 or 2 hydroxyl function(s), q, m and r are integral indices such that q=0 or 1, 0≤m≤2 and 4≤r≤13, p is an integral index such that 1≤p≤3, said manufacturing step comprising ammoniation of the carbonyl function of the unsaturated fatty acid or ester of natural origin to a nitrile function.

As unsaturated fatty acids or esters of natural origin corresponding to the above formula that are more particularly suitable for carrying out the invention, it is possible to use those mentioned above.

Ammoniation (nitrilation) can be carried out according to the method described above.

Optionally, a step of hydrolysis of the aforementioned unsaturated fatty ester of natural origin can be carried out before ammoniation.

Optionally, a step of dehydration of the aforementioned hydroxylated fatty acid of natural origin can be carried out before ammoniation.

According to one embodiment of the invention, the unsaturated fatty acid derivative comprises an unsaturation in position 11 ($\delta$-11) or 12 ($\delta$-12) or more relative to the nitrile or acid function, according to one or other of the variants of the method, preferably being selected from: 11-octadecenoic acid, vaccenic acid, 11-eicosenoic acid, gondoic acid, 12-hydroxystearic acid, 14-hydroxyeicosanoic acid or mixtures thereof.

Preferably, the unsaturated fatty acid derivative is a vaccenic acid (C18:1, $\delta$-11) comprising an unsaturation in position 11 relative to the acid function.

Also preferably, the unsaturated fatty acid derivative is a gondoic acid (C20:1, $\delta$-11) comprising an unsaturation in position 11 relative to the acid function.

The unsaturated fatty acid derivative can advantageously be a lesquerolic acid (C20:1, $\delta$-11, 14-OH) comprising an unsaturation in position 11 relative to the acid function.

According to one embodiment of the invention, the fatty acid derivative comprises more than 18 carbon atoms, preferably more than 20 carbon atoms.

Preferably, the fatty acid derivative comprises more than 18 carbon atoms, even more preferably more than 20 carbon atoms and comprises an unsaturation in position 11, 13 or 15 relative to the nitrile or acid function, according to one or other of the variants of the method.

Step of Oxidative Cleavage

The method for cleaving unsaturated fatty chains according to the invention comprises a step of oxidative cleavage in which at least one fatty acid derivative having at least one unsaturation such as those mentioned above is reacted in the liquid phase with hydrogen peroxide in the presence of a catalyst for activating the reaction of oxidative cleavage and molecular oxygen and in the absence of organic solvent.

Derivatives of saturated fatty acids can of course be present in the reaction mixture in addition to the unsaturated derivatives of fatty acid, without their being involved in the reaction of oxidative cleavage. This is notably the case when a natural oil is used as the source of unsaturated fatty acids, provided the latter comprises a mixture of various saturated and unsaturated acids.

According to one embodiment, the content of hydrogen peroxide in the liquid phase is in the range from 3 to 55 wt %, preferably from 4 to 50 wt %, or even from 5 to 45 wt % relative to the total weight of the liquid phase.

According to one embodiment, hydrogen peroxide is used in the form of an aqueous hydrogen peroxide solution whose concentration of hydrogen peroxide is in the range from 35 to 70 wt %, preferably from 40 to 70 wt %, notably from 50 to 70 wt % and more preferably from 60 to 70 wt %, relative to the total weight of said solution. It is advantageous to work at high concentration of hydrogen peroxide to limit the content of dilution water in the reaction mixture. However, excessively concentrating the hydrogen peroxide must be avoided, to limit the risks of explosion. The concentration of hydrogen peroxide can be controlled by any suitable means, for example by determination of $H_2O_2$, monitoring the acidity of the medium (to be correlated with the concentration of heminitrile produced), measurement of the water content, measurement of the amount of water evaporated, measurement of the amount of heat released, measurement of density, measurement of viscosity, measurement of the refractive index, UV, IR, Raman spectroscopy.

Hydrogen peroxide can be introduced sequentially into the reaction mixture or, preferably, continuously.

The molar ratio of hydrogen peroxide to the fatty acid derivative can range from 1:1 to 20:1, notably from 1:1 to 6:1, preferably from 1:1 to 3:1.

The catalyst for activating the reaction of oxidative cleavage (hereinafter: "the catalyst") can notably be selected from those disclosed in application WO 96/39373.

It will be possible in particular to use:

oxides of tungsten or molybdenum, compounds capable of releasing tungstate or molybdate ions in the reaction mixture (for example chlorides and sulfides)

oxides of niobium, vanadium, tantalum, titanium or yttrium, metal compounds capable of being converted to metal oxides or of releasing metal ions in the reaction mixture (for example chlorides and sulfides such as $MoS_2$, $MoS_3$ or $VCl_3$), the oxides $WO_2$, $Nb_2O_5$, $WO_3$ or $MoO_3$, tungstic acid mixed with molybdic acid, titanium dioxide ($TiO_2$), titanium oxalate ($Ti_2(C_2O_4)_3$), niobium oxide ($Nb_2O_5$), iron oxide ($Fe_2O_3$) or optionally with vanadium oxide ($V_2O_5$) or cobalt(II) chloride, tungstic acid, tungsten trioxide, molybdic acid, niobic acid, or niobium pentoxide.

Preferably, the catalyst is selected from the oxides of tungsten, molybdenum, niobium, vanadium, tantalum, titanium or yttrium, their inorganic oxy acids, their heteropolyacids, their alkaline salts, palladium derivatives, manganese derivatives, and mixtures thereof.

As manganese derivatives, we may mention for example acetates, chlorides, sulfates, bromides and nitrates. As palladium derivatives, we may mention acetates and sultates.

The catalyst is more preferably selected from: manganese sulfate ($MnSO_4$), palladium sulfate ($PdSO_4$), tungstic acid ($H_2WO_4$), the sodium salt of tungstic acid ($Na_2WO_4$) combined with phosphoric acid ($H_3PO_4$), molybdic acid ($H_2MoO_4$), the sodium salt of molybdic acid ($Na_2MoO_4$), hetero-polyacids such as $H_3[PMo_{12}O_{40}]$, $H_4[SiMo_{12}O_{40}]$, $H_4[SiW_{12}O_{40}]$, $H_3[PW_{12}O_{40}]$, $(NH_4)_{10}[H_2W_{12}O_{42}]$, sodium metavanadate ($Na_3VO_4$) or ammonium metavanadate (($NH_4)_3VO_4$) or an alkaline salt of the latter, or palladium sulfate ($PdSO_4$) combined with a hetero-polyacid such as those mentioned above.

The content of catalyst introduced in the liquid phase can range from 0.1 to 10 wt %, preferably from 0.5 to 5 wt %, relative to the total weight of the organic phase comprising the fatty acid derivative.

According to the invention, the reaction of oxidative cleavage is carried out in the presence of molecular oxygen in the liquid phase.

The molecular oxygen present in the step of oxidative cleavage can be in the form of molecular oxygen of high purity (content above 80 mol %, preferably above 90 mol %, ideally above 99 mol %) or in the form of air or else in the form of enriched air (i.e. with higher oxygen partial pressure than in air).

According to one embodiment of the invention, oxygen is present in the form of microbubbles dispersed in the liquid phase. This promotes gas-liquid contact and improves the rate of dissolution of the oxygen in the liquid. "Microbubbles" means bubbles whose average diameter is in the range from 1 micron to 3 mm, preferably from 100 microns to 3 mm, preferably from 500 microns to 1 mm. The oxygen microbubbles can be suitably maintained in the dispersed state in the reaction mixture for example by vigorous stirring, or else by using an auto-aspirating turbine, a Loop® reactor of the Buss ChemTech type, a microreactor, a "Spinning Disk Reactor", a "Rotating packed bed reactor" or a descending film contactor.

According to a particularly advantageous embodiment, the reaction of oxidative cleavage is carried out continuously (hydrogen peroxide, oxygen and the fatty acid derivative are injected continuously into the reactor in which the reaction of oxidative cleavage takes place) and molecular oxygen is injected in countercurrent to the stream of unsaturated fatty acid derivative and hydrogen peroxide. In this configuration, the reaction can be carried out in a column reactor, molecular oxygen being injected at the bottom of the reactor, and the fatty nitrile at the top. Hydrogen peroxide can be injected either at the top of the reactor, or at several points near the top of the reactor. The molecular oxygen, ascending in the column, entrains some of the water present and allows a high concentration of hydrogen peroxide to be maintained in the reactor. In this configuration it is advantageous to use air as the source of molecular oxygen.

According to one embodiment, oxygen and hydrogen peroxide are introduced concomitantly in the mixture of fatty nitrile and catalyst. Alternatively, the oxygen can be introduced immediately after or just before the hydrogen peroxide.

According to one embodiment of the invention, oxygen is injected into the reaction mixture at a pressure ranging from 0.2 bar to 50 bar, notably from 1 bar to 20 bar, preferably from 1 to 5 bar.

When oxygen is in the form of enriched air, notably at more than 80 mol % of oxygen, the oxygen partial pressure injected into the reaction mixture more preferably ranges from 5 to 20 bar.

According to one embodiment of the invention, the content of molecular oxygen is in the range from 100 to 5000 mol %, preferably from 110 to 4000 mol %, of the stoichiometry of the reaction of oxidative cleavage. Oxygen in excess advantageously allows a high concentration of $H_2O_2$ to be maintained in the reactor, especially if it is operating continuously.

According to one embodiment of the invention, the water evaporated is evacuated from the reaction mixture continuously during the reaction of oxidative cleavage.

According to one embodiment of the invention, the step of oxidative cleavage is carried out at a temperature ranging from 20° C. to 130° C., notably from 30° C. to 90° C., preferably from 50° C. to 90° C. Optionally, the reaction can be carried out in at least two successive temperature stages.

When the reaction is carried out under pressure, the temperature can be increased to speed up the reaction, while keeping the reaction mixture in the liquid phase.

According to one embodiment of the invention, the step of oxidative cleavage is carried out for a time ranging from 10 minutes to 30 hours, preferably from 30 minutes to 8 hours. In industrial conditions, it is desirable to reduce the reaction time, notably by increasing the pressure and temperature.

Subsequent Steps

When the step of oxidative cleavage is carried out on an unsaturated fatty nitrile, it is possible that the step of oxidative cleavage does not lead directly to a heminitrile mixed with an acid but to intermediates of the aldehyde-nitrile type (also called omega oxo-nitriles) mixed with an aldehyde. These compounds offer the advantage of being oxidized very easily in contact with molecular oxygen. Thus, after the step of oxidative cleavage, it will be possible to carry out an additional step called autoxidation, with the aim of converting the aldehyde-nitrile to heminitrile and the aldehyde to the corresponding acid.

Thus, according to one embodiment of the invention, the method further comprises a step of autoxidation in which the product obtained at the end of the oxidative cleavage step, or the aldehyde-nitrile and/or aldehyde isolated from the rest of the product, is brought into contact with molecular oxygen.

According to one embodiment of the invention, the autoxidation step is carried out by bubbling molecular oxygen or a gas mixture containing molecular oxygen in the liquid phase comprising the aldehyde-nitrile and the aldehyde obtained at the end of the oxidative cleavage step, optionally in the presence of the catalyst for activating the reaction of oxidative cleavage.

According to a particular embodiment of the invention, molecular oxygen of high purity, i.e. of purity above 80 mol %, preferably above 90 mol %, and even more preferably above 99 mol %, is used in the autoxidation step. Alternatively, air or else air enriched with molecular oxygen is used.

Preferably, the autoxidation step is carried out without adding solvent and/or without adding catalyst for activating the molecular oxygen. A slight improvement in yield of aldehyde is observed on adding traces of alkalies and/or of other metals as catalyst. For this autoxidation step, various methods can be used, and notably those described in patent documents U.S. Pat. No. 6,680,395, U.S. Pat. No. 6,696,582, U.S. Pat. No. 6,800,783, U.S. Pat. No. 7,138,544, U.S. Pat. No. 7,799,945, WO10108586, FR2769624. Preferably, when an alkaline catalyst is used, there is no longer hydrogen peroxide in the medium. According to a particularly advantageous embodiment of the method of the invention, the autoxidation step is carried out as in document U.S. Pat. No. 6,696,582, without catalyst, in two steps using two successive stages of increasing temperatures of oxidation, notably for controlling the exothermic effect of the reaction. Preferably, autoxidation is carried out in a microreactor, which offers the advantage of rapidly removing the heat of reaction.

In the case when the autoxidation step is carried out in the presence of catalyst, it is notably possible to use those described in patent documents U.S. Pat. No. 7,799,945 and U.S. Pat. No. 7,138,544. Typically, an alkaline catalyst (generally in the form of acid salt) and a co-catalyst taken from group IV to XII of the periodic table are used. The alkaline catalysts improve the areas of gas-liquid contact, and consequently the migration of oxygen in the medium. It is the amount of dissolved oxygen that determines the kinetics of the autoxidation reaction. It is not, however, essential to use these catalysts during autoxidation. The use of vigorous stirring or of a microreactor is generally sufficient to obtain very good gas-liquid contact, and therefore very good mass exchange.

Preferably, the autoxidation step is carried out at a partial pressure of molecular oxygen ranging from 1 bar to 50 bar, notably from 1 bar to 20 bar, preferably from 1 to 5 bar. When the molecular oxygen is in the form of enriched air (with higher partial pressure than in air) notably of purity above 80%, the partial pressure of the oxygen injected into the reaction mixture is preferably in the range from 5 to 20 bar.

Advantageously, oxygen is injected continuously into the liquid phase by bubbling, preferably in the form of a stream of air or of molecular oxygen. Oxygen injected in the form of microbubbles promotes gas-liquid contact and improves the rate of dissolution in the liquid. "Microbubbles" means bubbles as defined above. Any technique of dispersion can be used, and more particularly those mentioned above in relation to the step of oxidative cleavage.

Advantageously, the molar ratio of molecular oxygen to the nitrile-fatty acid is in the range from 3:2 to 100:2.

The reaction is generally stopped when oxygen has been passed through in excess, representing more than 100% of stoichiometry, preferably more than 110% of stoichiometry, preferably more than 120% of stoichiometry, or even more than 220% of stoichiometry. The molar ratio of oxygen to the nitrile-fatty acid is thus between 100% and 5000% of stoichiometry and preferably greater than 110%.

Advantageously, autoxidation is carried out at a temperature ranging from 0° C. to 100° C., preferably from 20° C. to 100° C., notably from 30° C. to 90° C., preferably from 40° C. to 80° C., optionally in 2 consecutive stages of increasing temperatures.

The invention also relates to the use of the method for cleaving unsaturated fatty chains that has just been described for the synthesis of amino acids, dinitriles, diamines, diacids, polyesters and/or polyamides.

According to the first variant of the method of the invention, the diacids obtained at the end of the oxidative cleavage step can be used in numerous applications including the preparation of polyesters, notably by copolymerization with di- or polyols, or the preparation of polyamides, notably by copolymerization with diamines. Preferably, the unsaturated fatty acid derivatives employed in the method according to the invention are selected so as to obtain the C10, C11, C12, C13, C14, and/or C15 diacids. It will be particularly beneficial to select the unsaturated fatty acid derivatives with the aim of obtaining PA11 and/or PA12.

According to the second variant of the method according to the invention, the heminitrile obtained at the end of the oxidative cleavage step can be used as a substrate for synthesis of an ω-amino acid. The heminitrile is for example submitted to a reaction of hydrogen reduction of its nitrile function and any C=C unsaturations present according to the following reaction scheme:

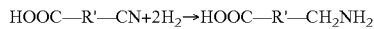

HOOC—R'—CN+2H$_2$→HOOC—R'—CH$_2$NH$_2$ where R' denotes an alkyl radical comprising from 4 to 13 carbon atoms or an alkylene radical comprising from 4 to 13 carbon atoms and from 0 to 2 unsaturations.

The reduction step can consist of a conventional hydrogenation. There are numerous catalysts that can be used, but preferably a Ru/SiC catalyst is used, or Raney nickel and cobalt. To promote formation of the primary amine, an ammonia partial pressure is used.

The ω-amino acid obtained can in its turn be used in numerous applications, including the preparation of polyamides. According to one embodiment, the method of the invention thus comprises a step of synthesis of polyamide by polymerization using said ω-amino acid. Preferably, the unsaturated fatty acid derivatives employed in the method according to the invention are selected so as to obtain PA9, PA11 and/or PA12.

The heminitrile obtained at the end of the method according to the invention can moreover be used as a substrate for synthesis of a dinitrile by a consecutive reaction with ammonia according to the following reaction scheme:

CN—R'—COOH+NH$_3$→CN—R'—CN+2H$_2$O where R' denotes an alkyl radical comprising from 4 to 13 carbon atoms or an alkylene radical comprising from 4 to 13 carbon atoms and from 0 to 2 unsaturations.

This ammoniation of the acid function can for example be carried out according to GB741739. The reaction can be carried out at high temperature, typically above 250° C., in the presence of a catalyst, which is generally a metal oxide and most often zinc oxide. Preferably, the starting compounds employed in the method according to the invention are selected so as to obtain the C9, C10, C11, C12 and/or C14 diamines.

The dinitriles obtained can moreover be hydrogenated to diamines. In this case, the starting compounds employed in the method according to the invention are preferably selected so as to obtain the C10, C12 and/or C14 diamines. These diamines can in their turn be used in numerous applications, including the preparation of polyamides, notably by reaction of these diamines with diacids.

The heminitrile obtained at the end of the method according to the invention can moreover be used as a substrate for synthesis of a diacid by hydrolysis of its nitrile function according to the following reaction scheme:

CN—R'—COOH+2H$_2$O→HOOC—R'—COOH+NH$_3$ where R' denotes an alkyl radical comprising from 4 to 13 carbon atoms or an alkylene radical comprising from 4 to 13 carbon atoms and from 0 to 2 unsaturations.

The hydrolysis is generally carried out in acid conditions.

The diacid obtained can be used in numerous applications, including the preparation of polyesters, notably by copolymerization with di- or polyols, or preparation of polyamides, notably by copolymerization with diamines. Preferably, the unsaturated fatty acid derivatives employed in the method according to the invention are selected so as to obtain the C10, C11, C12, C13, C14, and/or C15 diacids.

EXAMPLES

The following examples illustrate but do not limit the invention.

The following methods are used for the analyses. The composition of the organic phase is analyzed by gas chromatography (GC) with an HP 5890 series II chromatograph with HP5 column equipped with a FID detector. The content of hydrogen peroxide is analyzed by the permanganate assay method CEFIC PEROXYGENS H2O2 AM7157.

Example 1

Synthesis of Unsaturated Fatty Nitrile

A previously dried 0.5-L glass reactor, equipped with a mechanical stirrer, electric heating, a dephlegmator, a condenser, a dry-ice trap, and an ammonia feed system is charged with 250 g of 12-hydroxystearic acid. A catalytic charge of zinc oxide is added (0.0625% of the weight of fatty acid). Stirring of the reaction mixture is switched on, and then it is heated to 205° C. Then gaseous ammonia is fed in at a rate of 0.417 L/min·kg. The reaction mixture is heated to 300° C. Ammonia feed continues until the acidity index of the reaction mixture is below 0.1 mg KOH/g. The reaction time is about 10 h. At the end of reaction, the reaction mixture is cooled to 40° C. and the reactor is emptied. The product is purified by distillation and then analyzed by GC. The composition of the fatty nitrile obtained is shown in Table I.

TABLE I

| Fatty nitrile obtained from 12-hydroxystearic acid | wt % |
|---|---|
| C16:0 | 0.9 |
| C18:1 (δ-11 and δ-12) | 86.3 |
| C18:0 | 9.1 |
| C18:2 | 0.4 |
| C20:1 | 0.3 |
| C20:0 | 0.3 |

The product obtained is relatively clean owing to the absence of polyunsaturated acid in the starting acid.

Example 2

Oxidative Cleavage of Unsaturated Fatty Nitrile Chains

Test 2.1 (Comparative) Oxidative Cleavage in the Absence of Oxygen

A 250-cm$^3$ double-jacket reactor with a mechanical stirrer is charged with 25 g of the fatty nitrile synthesized in example 1 and 250 mg of tungstic acid ($H_2WO_4$; Merck 98%), then stirred and heated to 70° C., the temperature being maintained by thermostatically controlled circulation of water. 7 g of aqueous hydrogen peroxide solution ($H_2O_2$ concentration equal to 70 wt %) is added dropwise by a peristaltic pump over the space of 20 minutes. After reaction for 2 h, the aqueous phase is separated from the organic phase and replaced with 7 g of fresh hydrogen peroxide solution ($H_2O_2$ concentration equal to 70 wt % %) containing 250 mg of tungstic acid. Renewal of the aqueous phase is repeated similarly after 17 h, 19 h, 21 h and 23 h, then the reaction is stopped after 25 h. In total, 6 additions of hydrogen peroxide were made in this way, for a total amount of hydrogen peroxide introduced of 42 g. The last aqueous phase is separated from the organic phase. The remaining organic phase is washed several times with demineralized water until hydrogen peroxide disappears from the wash water and then it is dried under vacuum and analyzed by GC.

Test 2.2 (According to the Invention) Oxidative Cleavage in the Presence of Oxygen The test is carried out as in test 2.1 except that at the end of each addition of aqueous hydrogen peroxide solution (initially and then after reaction for 2 h, 17 h, 19 h, 21 h and 23 h) air is bubbled into the liquid reaction mixture with stirring at 500 rev/min. The air is supplied via the reactor bottom valve at an air flow rate ranging from 100 to 120 mL/min. As in test 2.1, the organic phase, once washed and dried, is analyzed by GC.

The results are given in Table II. The concentrations of products are expressed in mmol/g.

Comparison of tests 2.1 and 2.2 shows that concomitant addition of oxygen and hydrogen peroxide is favorable to the reaction of oxidative cleavage of a fatty nitrile since we observe an increase in the amount of cleavage products comprising an acid function. The amount of heminitriles (11-cyano-undecanoic acid (C12) and 10-cyano-decanoic acid (C11)) increases considerably.

Example 2bis

Oxidative Cleavage of Unsaturated Fatty Acid Chains

Test 2bis.1 (Comparative) Oxidative Cleavage in the Absence of Oxygen

A 250-cm$^3$ double-jacket reactor with a mechanical stirrer and a condenser is charged with 32.4 g of a mixture of fatty acids comprising predominantly oleic acid (C18:1) (Fluka, 72.5%) and 334 mg of tungstic acid ($H_2WO_4$; Merck 98%), then stirred and heated to 90° C. This temperature is maintained by thermostatically-controlled circulation of water/glycol. 36.5 g of aqueous hydrogen peroxide solution ($H_2O_2$ concentration equal to 50 wt %) is added dropwise by a peristaltic pump over the space of 5 h. The reaction is stopped after 24 h. The aqueous phase is separated from the organic phase. The organic phase is washed with demineralized water several times until hydrogen peroxide disappears from the wash water, then it is dried under vacuum and analyzed by GC.

Test 2bis.2 (According to the Invention) Oxidative Cleavage in the Presence of Oxygen A 250-cm$^3$ double-jacket reactor with a mechanical stirrer and a condenser is charged with 32.6 g of a mixture of fatty acids comprising predominantly oleic acid (C18:1) (Fluka, 72.5%) and 305 mg of tungstic acid ($H_2WO_4$; Merck 98%), then stirred and heated to 90° C. This temperature is maintained by thermostatically-controlled circulation of water/glycol. 36.6 g of aqueous hydrogen peroxide solution ($H_2O_2$ concentration equal to 50 wt %) is added dropwise by a peristaltic pump. After one hour, an air flow rate of 400 mL/min is circulated in the reaction mixture via a Teflon tube. Hydrogen peroxide solution is added dropwise for a total time of 5 h, then the reaction is stopped after 24 h. The aqueous phase is separated from the organic phase. The organic phase is washed with demineralized water several times until hydrogen peroxide disappears from the wash water, then it is dried under vacuum and analyzed by GC.

The results are given in Table III. The concentrations of products are expressed in mmol/g.

TABLE II

| | Composition (mmol/g) | | | | | | | |
|---|---|---|---|---|---|---|---|---|
| Example No. | C16:0 | C18:1 | Hexanoic acid C6 | Heptanoic acid C7 | 11-cyano-undecanoic acid C12 | 10-cyano decanoic acid C11 | 11-oxo-undecanenitrile C11 | 12-oxo-dodecanenitrile C12 |
| 1 | 0.043 | 3.14 | — | — | — | — | — | — |
| 2.1 ($H_2O_2$) | 0.034 | 0.01 | 0.293 | 0.348 | 0.340 | 0.371 | 0.420 | 0.378 |
| 2.2 ($H_2O_2 + O_2$) | 0.034 | 0.02 | 0.323 | 0.383 | 0.543 | 0.532 | 0.387 | 0.334 |

TABLE III

| Example No. | Composition (mmol/g) | | | | |
|---|---|---|---|---|---|
| | Palmitic acid C16:0 | Oleic acid C18:1 | Nonanoic acid | Azelaic acid | 9-oxo-nonanoic acid |
| Mixture of fatty acids | 0.167 | 2.538 | — | — | — |
| 2.3 ($H_2O_2$) | 0.124 | 0.00 | 0.272 | 0.235 | 0.004 |
| 2.4 ($H_2O_2 + O_2$) | 0.134 | 0.00 | 0.417 | 0.392 | 0.027 |

Comparison of tests 2.3 and 2.4 shows that concomitant addition of oxygen and hydrogen peroxide is favorable for the reaction of oxidative cleavage of a fatty acid since we observe an increase in the amount of cleavage products comprising an acid function. The amount of diacid (azelaic acid) increases considerably.

Test 2bis.3 (According to the Invention) Oxidative Cleavage in the Presence of Oxygen A 250-cm³ double-jacket reactor with a mechanical stirrer and a condenser is charged with 120.9 g of a mixture of fatty acids comprising predominantly eicosenoic acid (C20:1) (Lutacid Ee, K&H Chemicals, composition shown in Table IV) and 6.0 g of tungstic acid ($H_2WO_4$; Merck 98%), then stirred and heated to 80° C. This temperature is maintained by thermostatically-controlled circulation of water/glycol. A valve is provided between the reactor and the condenser for evacuation of reflux liquid. 168.0 g of aqueous hydrogen peroxide solution ($H_2O_2$ concentration equal to 65 wt %) is added dropwise by a peristaltic pump for a total time of 6 h as follows: at the end of the first hour, an air flow rate of 400 mL/min is circulated in the reaction mixture using a Teflon submerged tube; between the first and sixth hour inclusive, the valve is opened to allow evacuation of reflux liquid; after the sixth hour, the valve is closed and the air flow rate is decreased to 200 mL/min. The reaction is stopped after 24 h. The aqueous phase is separated from the organic phase. The organic phase is washed with demineralized water several times until hydrogen peroxide disappears from the wash water, then it is dried under vacuum and analyzed by GC.

The results are given in Table V. The concentrations of products are expressed in mmol/g.

TABLE IV

| Composition of the mixture of fatty acids | wt % |
|---|---|
| C18:1 | 21.38 |
| C20:1 | 46.29 |
| C20:0 | 4.29 |
| C22:1 | 12.69 |

TABLE V

| Example No. | Composition (mmol/g) | | | | | |
|---|---|---|---|---|---|---|
| | Eicosanoic acid C20:0 | Eicosenoic acid C20:1 | Nonanoic acid | Azelaic acid | Undecanedioic acid | Brassylic acid |
| Mixture of fatty acids | 0.137 | 1.491 | — | — | — | — |
| 2bis.3 ($H_2O_2 + O_2$) | 0.110 | 0.00 | 0.533 | 0.152 | 0.335 | 0.154 |

Example 3

Reduction of the Heminitriles to Obtain Amino Acids

Example 2.2 is reproduced, continuing addition of air for 24 hours at 80° C., and measuring the contents of cyanoacids and of oxonitrile. As the cyanoacids are soluble in acetic acid, the product of the cleavage reaction is extracted with an acetic acid/water mixture, then this solvent and the light acids (hexanoic and heptanoic) are evaporated. The product is recrystallized once from acetic acid.

An Ru/SiC catalyst is put in a 500-ml stainless steel autoclave equipped with an electromagnetic stirrer. A solution containing 5 g of the mixture of 11-cyanoundecanoic acid and 10-cyanodecanoic acid obtained according to the invention and of mixed solvent of 140 ml of n-propanol and 140 ml of ammonia solution at 28 wt % ammonia is put in the autoclave. After purging the reactor with nitrogen several times, the reactor is pressurized to 35 bar with hydrogen. The reactor is then heated to 110° C. and the stirring and the temperature are kept constant for 1 h 30 min. The reaction then no longer consumes hydrogen and the autoclave temperature is lowered to 70° C., then the pressure is reduced to atmospheric pressure and a colorless liquid is withdrawn. The solvent is then evaporated at about 60° C. under vacuum, and white crystals (4 g) of mixture of 11-aminoundecanoic acid and 12-aminododecanoic acid are recovered.

The invention claimed is:

1. A method for cleaving unsaturated fatty chains comprising a step of oxidative cleavage in which at least one fatty acid derivative having at least one unsaturation is reacted in the liquid phase with hydrogen peroxide in the presence of a catalyst for activating the reaction of oxidative cleavage and of molecular oxygen and in the absence of organic solvent.

2. The method as claimed in claim 1, wherein said fatty acid derivative having at least one unsaturation is selected from: a fatty acid, a fatty acid ester, a triglyceride, an ester of fatty acid and fatty alcohol or mixtures thereof, so as to obtain at least one diacid at the end of said oxidative cleavage step.

3. The method as claimed in claim 1, wherein said fatty acid derivative is a fatty nitrile corresponding to the formula:

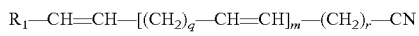

$R_1$—CH=CH—[($CH_2$)$_q$—CH=CH]$_m$—($CH_2$)$_r$—CN where $R_1$ is H or an alkyl radical comprising from 1 to 11 carbon atoms optionally comprising a hydroxyl function and/or a terminal nitrile function, q, in and r are integers such that q=0 or 1, 0≤m≤2 and 4≤r≤13, or mixtures thereof, so as to obtain, at the end said oxidative cleavage step, at least one nitrile-acid of formula:

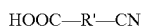

HOOC—R'—CN where R' is an alkyl radical comprising from 4 to 13 carbon atoms or an alkylene radical comprising from 4 to 13 carbon atoms and from 0 to 2 unsaturations.

4. The method as claimed in claim 3, further comprising a step of manufacturing said fatty nitrile from an unsaturated fatty acid or ester of natural origin of formula:

$$(R_1-CH=CH-[(CH_2)_q-CH=CH]_m-(CH_2)_r-COO-)_p-G$$

where p is an integer such that $1 \leq p \leq 3$,

G is H, an alkyl radical with 1 to 11 carbon atoms or a radical comprising 2 or 3 carbon atoms bearing 1 or 2 hydroxyl function(s), said manufacturing step comprising ammoniation of the carbonyl function of the unsaturated fatty acid or ester of natural origin to a nitrile function.

5. The method as claimed in claim 3, further comprising hydrogenation of said nitrile-acid leading to an ω-amino acid of formula:

$$HOOC-R'CH_2NH_2.$$

6. The method as claimed in claim 2, further comprising a step of polyamide synthesis by polymerization using said diacid.

7. The method as claimed in claim 1, wherein during the step of oxidative cleavage, oxygen is present in the form of microbubbles dispersed in the liquid phase.

8. The method as claimed in claim 1, wherein the catalyst for activating the reaction of oxidative cleavage is selected from oxides of tungsten, molybdenum, niobium, vanadium, tantalum, titanium or yttrium, their inorganic oxy acids, their heteropolyacids, their alkaline salts, palladium derivatives, manganese derivatives, and mixtures thereof.

9. The method as claimed in claim 1, wherein the step of oxidative cleavage is carried out at an oxygen pressure ranging from 0.2 bar to 50 bar.

10. The method as claimed in claim 1, wherein the content of molecular oxygen is in the range from 100 to 5000% of the stoichiometry of the reaction of oxidative cleavage.

11. The method as claimed in claim 1, wherein the content of hydrogen peroxide in the liquid phase is in the range from 3 to 55 wt % to the total weight of the liquid phase.

12. The method as claimed in claim 1, wherein during the step of oxidative cleavage the molar ratio of hydrogen peroxide to the fatty acid derivative is in the range from 1:1 to 20:1.

13. The method as claimed in claim 1, wherein the step of oxidative cleavage is carried out at a temperature ranging from 20° C. to 130° C.

14. The method as claimed in claim 1, wherein the acid derivative comprises at least one unsaturation in position 11, 12 or more relative to its nitrile or acid function, selected from: 11-octadecenoic acid, vaccenic acid, 11-eicosenoic acid, gondoic acid, 12-hydroxystearic acid, 14-hydroxyeicosanoic acid or mixtures thereof.

15. The method as claimed in claim 5, further comprising a step of polyamide synthesis by polymerization using said ω-amino acid.

16. The method as claimed in claim 1, wherein the step of oxidative cleavage is carried out at an oxygen pressure ranging from 1 bar to 20 bar.

17. The method as claimed in claim 1, wherein the step of oxidative cleavage is carried out at an oxygen pressure ranging from 1 to 5 bar.

18. The method as claimed in claim 1, wherein the content of molecular oxygen is in the range from 110 to 4000%, of the stoichiometry of the reaction of oxidative cleavage.

19. The method as claimed in claim 1, wherein the content of hydrogen peroxide in the liquid phase is in the range from 4 to 50 wt % relative to the total weight of the liquid phase.

20. The method as claimed in claim 1, wherein the content of hydrogen peroxide in the liquid phase is in the range from 5 to 45 wt % relative to the total weight of the liquid phase.

21. The method as claimed in claim 1, wherein during the step of oxidative cleavage the molar ratio of hydrogen peroxide to the fatty acid derivative is in the range from 1:1 to 6:1.

22. The method as claimed in claim 1, wherein during the step of oxidative cleavage the molar ratio of hydrogen peroxide to the fatty acid derivative is in the range from 1:1 to 3:1.

23. The method as claimed in claim 1, wherein the step of oxidative cleavage is carried out at a temperature ranging from 20° C. to 130° C.

24. The method as claimed in claim 1, wherein the step of oxidative cleavage is carried out at a temperature ranging from 50° C. to 90° C.

* * * * *